United States Patent [19]

Fawzi

[11] Patent Number: 4,609,396

[45] Date of Patent: Sep. 2, 1986

[54] QUINOXALINYLOXY ETHERS AS SELECTIVE WEED CONTROL AGENTS

[75] Inventor: Maged M. Fawzi, Wilmington, Del.

[73] Assignee: E. I. Du Pont de Nemours and Company, Wilmington, Del.

[21] Appl. No.: 161,940

[22] Filed: Jun. 23, 1980

[51] Int. Cl.[4] .................. A01N 43/60; C07D 241/44; C07D 401/12; C07D 403/12

[52] U.S. Cl. ........................................ 71/92; 544/116; 544/354; 544/171; 544/391; 560/39; 540/599

[58] Field of Search .................. 544/116, 354; 71/88, 71/92; 260/243.3

[56] References Cited

U.S. PATENT DOCUMENTS

| | | | |
|---|---|---|---|
| 3,040,046 | 6/1962 | Sasse | 544/354 |
| 3,752,812 | 8/1973 | Abushanab | 544/354 |
| 3,928,608 | 12/1975 | Cox et al. | 544/354 |
| 4,083,714 | 4/1978 | Takahashi | 546/302 |
| 4,236,912 | 12/1980 | Johnston | 71/94 |
| 4,391,628 | 7/1983 | Rempfler | 544/354 |

FOREIGN PATENT DOCUMENTS 3004770 8/1980 Fed. Rep. of Germany .

OTHER PUBLICATIONS

Hondte et al, Chem. Abs., 88, 190816h (1976).
Nordmann, Chem. Abs., 78, 29817 (1972).

*Primary Examiner*—Mark L. Berch

[57] ABSTRACT

This invention relates to herbicidal quinoxalinyloxy ethers, herbicidal compositions containing said ethers, and methods of using said compounds as herbicides.

9 Claims, No Drawings

QUINOXALINYLOXY ETHERS AS SELECTIVE WEED CONTROL AGENTS

TECHNICAL FIELD

This invention relates to quinoxalinyloxy ethers which are useful as selective weed control agents. The compounds are especially useful for controlling grass weeds in broadleaf crops such as soybeans.

The presence of undesirable vegetation causes substantial damage to useful crops, especially agricultural products that satisfy man's basic food and fiber needs, such as cotton, soybeans, beans and the like. The current population explosion and concomitant world food and fiber shortage underlie the need for improvements in the efficiency of producing these crops. Preventing or minimizing the loss of a portion of such valuable crops by killing of inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

It has now been found that the novel compounds of Formula I are useful as pre- and post-emergence herbicides.

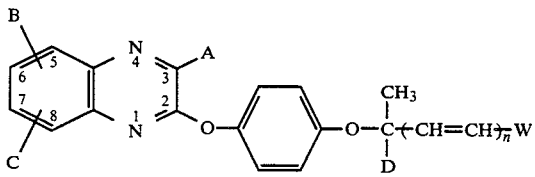

where
A is H or $C_1$-$C_4$ alkyl;
B is H, Cl, Br, F, $CF_3$, $OCH_3$ or $NO_2$;
C is H, $CH_3$, Cl, Br or F;
W is CN or

R is Cl, $XR_1$, $NR_2R_3$, OH or OM;
$R_1$ is $C_1$-$C_4$ alkyl,

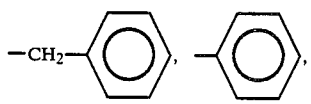

$C_5$-$C_8$ cycloalkyl, $-CH_2CH_2OCH_3$, $-CH_2CH_2OCH_2CH_3$ or $-CH_2CH_2CH_2OCH_3$, $C_3$-$C_4$ alkenyl, $C_3$-$C_4$ alkynyl or $C_3$-$C_4$ alkenyl or alkynyl optionally substituted with one Cl;
X is O or S;
M is an agriculturally suitable salt;
$R_2$ is H, $C_1$-$C_4$ alkyl, $C_5$-$C_8$ cycloalkyl,

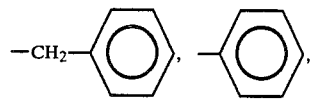

$-OCH_3$, $C_3$-$C_4$ alkenyl or $-CH_2CH_2NR_4R_5$ where $R_4$ and $R_5$ are independently methyl or ethyl;
$R_3$ is H or $C_1$-$C_4$ alkyl; or
$R_2$ and $R_3$ may be taken together to be $-(CH_2)_2-O-(CH_2)_2-$, $-(CH_2)_4-$, $-(CH_2)_5-$, $-(CH_2)_6-$ or

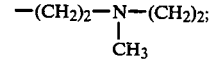

n is 0 or 1;
D is H or $CO_2R_1$;
provided that:
(a) when n=1, then D=H; and
(b) $R_2$ and $R_3$ together contain no more than 6 carbon atoms.

DETAILED DESCRIPTION

Preferred in order of increasing activity and/or increasingly more favorable cost are those compounds of Formula I where
(1) A is H or $CH_3$.
(2) Compounds of preference (1) where A is H.
(3) Compounds of preference (2) where B and C are independently H, F, Cl or Br.
(4) Compounds of preference (3) where B and C are at positions 6 and 7 of the quinoxaline ring.

More preferred for their exceptionally high activity and/or exceptionally favorable cost are those compounds of preferrence (4) where R is $OR_1$, OH or OM.

The following compounds are specifically preferred for the same reasons:
Methyl 2-[4-(6(or 7)-chloro-2-quinoxalinyloxy)phenoxy]propanoate;
Methyl 2-[4-(2-quinoxalinyloxy)phenoxy]propanoate; and
Methyl 2-[4-(6,7-dichloro-2-quinoxalinyloxy)phenoxy]propanoate.

Some of the compounds falling within the scope of this invention may be optically active. These optically active compounds have the potential for being more potent herbicides than the racemates.

SYNTHESIS

The various compounds of Formula I can be prepared via a number of different routes, depending on the definition of n and D.

(a) Compounds of Formula I where n=O and D=H.
Compounds of Formula I where n=O, D=H, W=$COXR_1$, X=O and R=$C_1$-$C_4$ alkyl (represented by Formula IIa) can be prepared by combining, preferably in equimolar amounts, a 2-chloroquinoxaline and the alkai metal salt of alkyl 2-(4-hydroxyphenoxy)-propanoate as illustrated below:

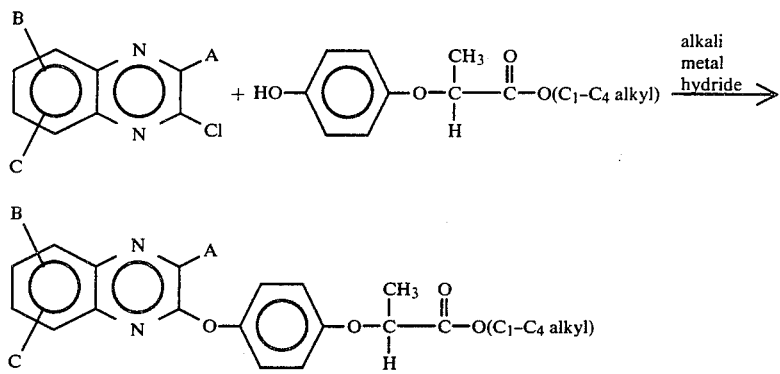

Suitable solvents for this reaction include dimethylformamide, dimethylsulfoxide, diglyme and methylethylketone. The reaction is preferably carried out at a temperature between about 25° and about 130° C. The esters of Formula IIa are useful starting materials for preparing other compounds of this invention.

The 2-chloroquinoxalines used in this reaction can be prepared by methods known in the art. Glyoxylic acid, substituted glyoxylic acid or an alkyl ester of glyoxylic acid is combined with a substituted o-phenylenediamine in ethanol to yield a 2-hydroxyquinoxaline, as described in *J.A.C.S.* 71, 6 (1949). The 2-hydroxyquinoxaline is treated with phosphorous oxychloride as described in *J.C.S.*, 519 (1948) or *Bull. Soc. Chem. France*, 356 (1963), to give the desired 2-chloroquinoxalines. The disclosures of the above-cited references are hereby incorporated by reference.

The alkyl 2-(4-hydroxyphenoxy)propanoates used in the reaction are known in the art and can be prepared in a two-step process from commercially available compounds. First, 4-benzyloxyphenol is alkylated by reaction with an alkyl bromopropanoate. The product is hydrogenated in the presence of a palladium over carbon catalyst to yield the desired compound.

Compounds of Formula I where W=COR and R=OH (represented by Formula IIb) can be prepared by hydrolysis of an ester of Formula IIa:

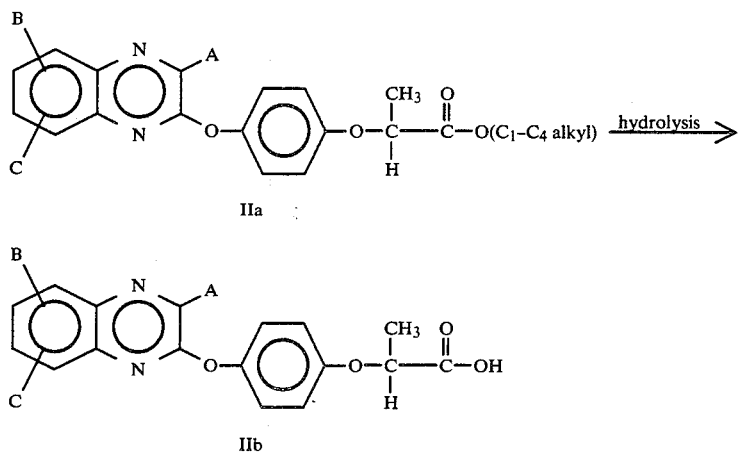

Either acid hydrolysis with, for example, dilute hydrochloric or sulfuric acid, or basic hydrolysis with, for example, sodium hydroxide or potassium hydroxide, followed by acidification with dilute acid yields the acids of Formula IIb. These acids may be treated with excess thionyl chloride to yield the acid chlorides of Formula II-c, where W=COR and R=Cl:

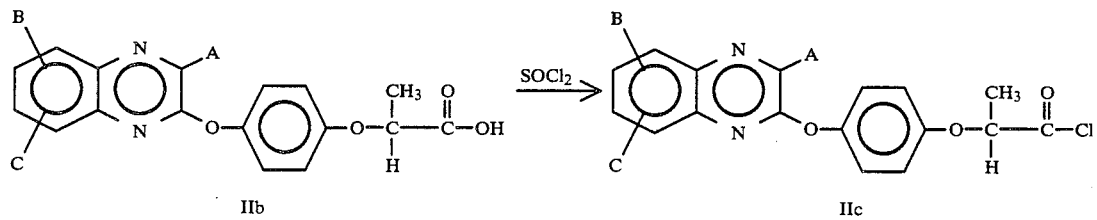

Compounds of Formula I where W=COR and $R=NR_2R_3$ (represented by Formula IId) can be prepared by combining an acid chloride of Formula IIc with two moles of the appropriate amine:

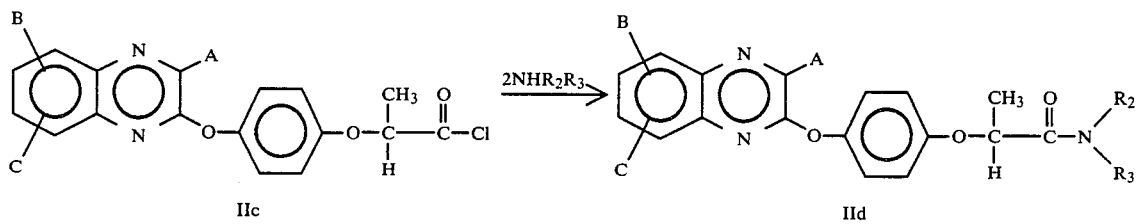

IIc → IId

The acid chloride and amine are preferably combined at or below ambient temperature in a solvent such as tetrahydrofuran or methylene chloride.

Compounds of Formula I where W=COR and R=$XR_1$ (represented by Formula IIe) are prepared by combining an acid chloride of Formula IIc with the appropriate alcohol, thiol, phenol or thiophenol in the presence of an equimolar amount of an acid acceptor:

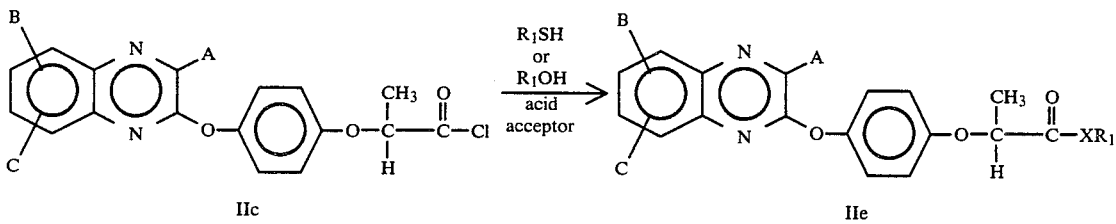

IIc → IIe

Suitable acid acceptors include pyridine and N,N-dimethylaniline. The reaction is preferably run under a nitrogen atmosphere at a temperature of from about 0° to about 40° C.

Compounds where W=CN can be prepared by the condensation of the appropriate quinoxaline with the alkali metal salt of 2-(4-hydroxyphenoxy)propionitrile. Dimethylformamide is an example of a suitable solvent.

Agriculturally suitable salts of the acids of Formula IIb are useful herbicides and include, but are not limited to, ammonium, sodium lithium, potassium, calcium, magnesium, barium and quaternary ammonium salts. These salts can be prepared by a number of known methods. For example, metal salts can be prepared by treating compounds of Formula IIb with a solution of an alkali or alkaline earth metal salt having a sufficiently basic anion (e.g., hydroxide, alkoxide, carbonate or hydride). Ammonium, amine and quaternary ammonium salts can be made by similar techniques.

(b) Compounds of Formula I where n=1 and D=H.

Compounds of Formula I where n=1, D=H, W=$COXR_1$, X=O and $R_1$=$C_1$-$C_4$ alkyl (represented by Formula IIIa) can be prepared as outlined below:

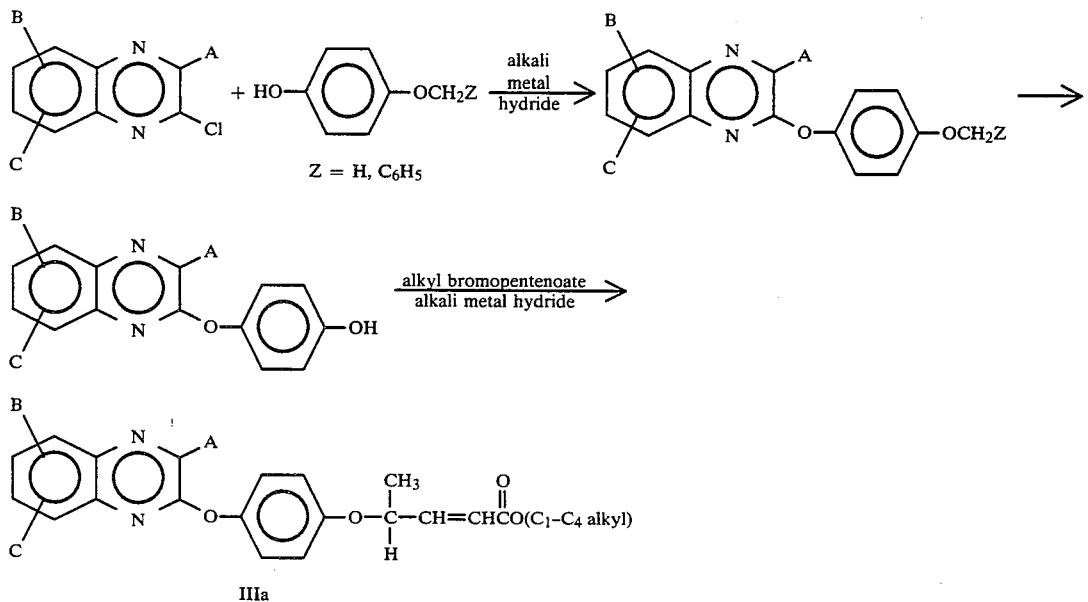

IIIa

A 2-chloroquinoxaline is condensed with 4-benzyloxyphenol or 4-methoxyphenol in the presence of sodium methoxide or an alkali metal hydride. Next, the methyl or benzyl group is removed by methods known in the art, for example those described in Belgian Pat. No. 868,875 or Tetrahedron 24, 2289 (1968), both herein incorporated by reference, to yield a 2-(4-hydroxyphenoxy)quinoxaline. Interaction of this product with an alkyl bromopentenoate in the presence of an alkali metal hydride yields the desired esters.

The esters of Formula IIIa may be used to prepare the acids, acid chlorides, amides and esters of this invention as well as the salts of these compounds, by methods identical to those used to prepare the corresponding compounds of Formulas IIb–IIe. Compounds of this type where W=CN can be prepared by the interaction of the alkali metal salt of the 2-(4-hydroxyphenoxy)-quinoxaline with 4-bromo-2-pentenenitrile.

(c) Compounds of Formula I where n=O and $D=CO_2R_1$.

This group of compounds, represented by Formula IV, where W=CN,

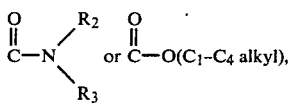

can be prepared in either of two ways:

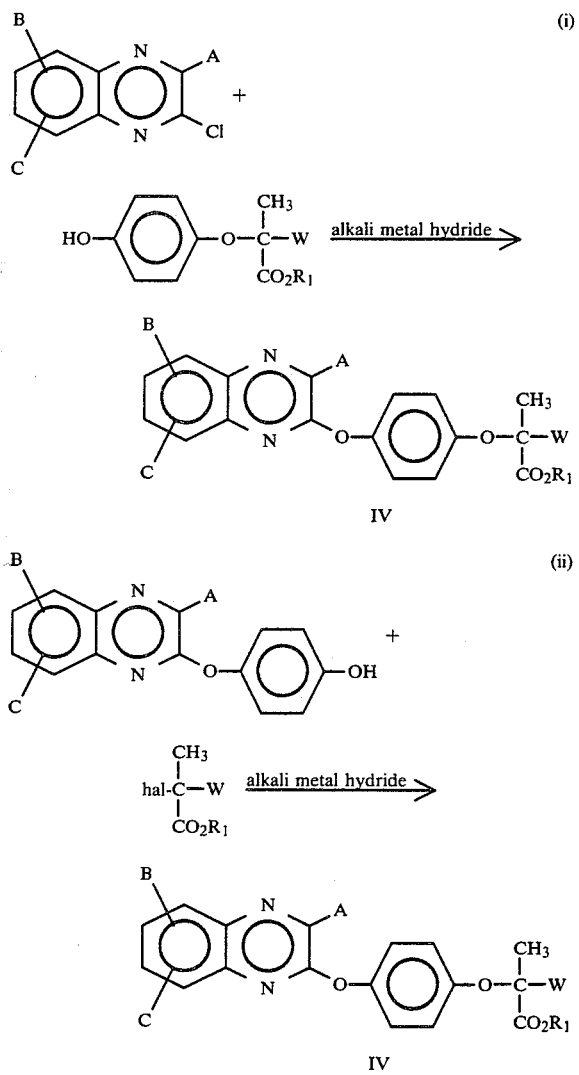

In process (i), a substituted 2-chloroquinoxaline and the alkali metal salt of the appropriate phenol are combined, preferably at a temperature between about 25° and about 130° C. Suitable solvents include DMF. The phenols can be prepared by procedures similar to those outlined above in relation to the preparation of alkyl 2-(4-hydroxyphenoxy)propanoates.

In process (ii), the alkali metal salt of the appropriate 2-(4-hydroxyphenoxy)quinoxaline is reacted with a halogenated malonic acid derivative.

Compounds where

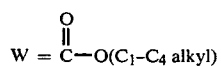

may be used to prepare the acids, acid chlorides and esters of this invention as well as salts of these compounds by methods similar to those used to prepare the corresponding compounds of Formulae IIb, IIc and IIe.

The following examples illustrate the preparation of some of the compounds of the invention.

EXAMPLE 1

Methyl 2-[4-(2-quinoxalinyloxy)phenoxy]propanoate

In a nitrogen atmosphere, a solution of 5.9 g (0.03 mole) methyl 2-(4-hydroxyphenoxy)propanoate in 20 cc of dimethylformamide was added dropwise at about 15° C. to 1.5 g (0.03 mole) 57% sodium hydride in 20 cc dimethylformamide. When the evolution of hydrogen ceased, 4.9 g (0.03 mole) 2-chloroquinoxaline was added and the reaction mixture was heated at 130° C. for 4 hours. After standing overnight at room temperature, the reaction mixture was poured into about 100 cc of cold water. The precipitated solid was filtered and crystallized from methanol to give 4.2 g of product, m.p. 110°–115°.

NMR (DMSO)δ: 1.5 (d, 3H), 3.7 (s, 3H), 4.9 (q, 1H), 7 (d, 2H), 7.3 (d, 2H), 7.45–8.2 (m, 4H), 8.9 (s, 1H).

EXAMPLE 2

Methyl 2-[4-(6,7-dichloro-2-quinoxalinyloxy)phenoxy]propanoate

In a nitrogen atmosphere, a solution of 3.9 g (0.02 mole) methyl 2-(4-hydroxyphenoxy)propanoate in 20 cc of dimethylformamide was added dropwise at about 15° C. to a suspension of 0.8 g sodium hydride in 10 cc dimethylformamide. When the evolution of hydrogen ceased, 4.7 g of (0.02 mole) 2,6,7-trichloroquinoxaline was added and the reaction mixture was heated for 5 hours at ~130° C. Filtering the reaction mixture yielded a small amount of insoluble material. The filtrate was poured into approximately 200 cc of ice-water. Sodium chloride was added to the solution which was then extracted with 1200 cc of ether (4×300). The ethereal extracts were combined and dried over magnesium sulfate. The ether was removed under vacuum and the crude product was crystallized from $CH_3OH$. Yield 2.8 g, m.p. 100°–105°.

NMR (CDCl$_3$)δ: 1.7 (d, 3H), 3.8 (s, 3H), 4.75 (q, 1H), 7 (d, 2H), 7.25 (d, 2H), 8 (s, 1H), 8.3 (s, 1H), 8.8 (s, 1H).

EXAMPLE 3

Methyl 2-[4-(6 or 7)chloro-2-quinoxalinyloxy)phenoxy]propanoate

The named compound was prepared from 2,6- or 7-dichloroquinoxaline and methyl 2-(4-hydroxyphenoxy)propanoate by the procedure described under Example 2. The crude product was crystallized from $CH_3OH$, m.p. 108°–111°.

NMR (CDCl$_3$)δ: 1.7 (d, 3H), 3.8 (s, 3H), 4.8 (q, 1H), 7 (d, 2H), 7.3 (d, 2H), 7.4–8.2 (m, 3H), 8.8 (s, 1H).

Following the teachings of Examples 1 and 2 and by substituting an appropriate 2-chloroquinoxaline and an appropriate alkyl 2-(4-hydroxyphenoxy)propanoate, the compounds in Table I can be prepared.

TABLE I

Structure: quinoxaline with substituents B, C on benzo ring, A on position 3, linked via O-phenyl-OCH(CH$_3$)-CO$_2$R$_1$

| A | B | C | R$_1$ |
|---|---|---|---|
| H | 6-CF$_3$ | H | CH$_3$ |
| H | 7-Br | H | CH$_3$ |
| H | 6-F | H | CH$_3$ |
| H | 7-F | H | CH$_3$ |
| H | 6-Br | H | CH$_3$ |
| H | 7-OCH$_3$ | H | CH$_3$ |
| H | 7-CH$_3$ | H | CH$_3$ |
| H | 6-NO$_2$ | H | CH$_3$ |
| H | 7-Cl | 5-CH$_3$ | n-C$_3$H$_7$ |
| H | 6-CF$_3$ | 8-Cl | CH$_3$ |
| H | 6-Cl | 8-Cl | CH$_3$ |
| H | 6-OCH$_3$ | 8-Cl | CH$_3$ |
| H | 5-Br | 7-Br | CH$_3$ |
| H | 5-F | 7-Cl | n-C$_4$H$_9$ |
| H | 6-Cl | H | C$_2$H$_5$ |
| H | 7-Cl | H | i-C$_3$H$_7$ |
| H | 8-F | H | t-C$_4$H$_9$ |
| CH$_3$ | 6-Cl | H | CH$_3$ |
| CH$_3$ | 6-Cl | 7-Cl | CH$_3$ |
| CH$_3$ | 6-CF$_3$ | H | CH$_3$ |
| C$_2$H$_5$ | 6-Cl | H | CH$_3$ |
| C$_4$H$_9$ | 6-Cl | H | CH$_3$ |

EXAMPLE 4

2-[4-(2-Quinoxalinyloxy)phenoxy]propanoic acid 3.2 g (0.01 mole) Methyl 2-[4-(2-quinoxalinyloxy)phenoxy]propanoate was added to a solution of 0.7 g (0.01 mole) potassium hydroxide in 5 cc water and 60 cc methanol. The mixture was stirred at room temperature overnight and then filtered to remove a small amount of insoluble material. The methanol was removed under vacuum. Ice and hydrochloric acid were added to the mixture until it was acidic (pH~2). The precipitated acid was filtered and purified by redissolution into saturated sodium bicarbonate solution, reprecipitation by acidification with dilute hydrochloric acid and crystallization from methanol. Yield 0.7 g, m.p. 137°-141°.

NMR (CDCl$_3$-DMSO)δ: 1.7 (d, 3H), 4.8 (q, 1H), 7.05 (d, 2H), 7.3 (d, 2H), 7.4–8.4 (m, 4H), 8.8 (s, 1H).

By hydrolysis of the appropriate ester employing procedures similar to that described above, the acids listed in Table II can be prepared.

TABLE II

Structure: quinoxaline with substituents B, C on benzo ring, A on position 3, linked via O-phenyl-OCH(CH$_3$)-CO$_2$H

| A | B | C |
|---|---|---|
| H | 6-CF$_3$ | H |
| H | 7-Br | H |
| H | 6-F | H |
| H | 7-F | H |
| H | 6-Br | H |
| H | 7-OCH$_3$ | H |
| H | 7-CF$_3$ | H |
| H | 6-NO$_2$ | H |
| H | 7-Cl | 5-CH$_3$ |
| H | 6-CF$_3$ | 8-Cl |
| H | 6-Cl | 8-Cl |
| H | 6-OCH$_3$ | 8-Cl |
| H | 5-Br | 7-Br |
| H | 5-F | 7-Cl |
| H | 6-Cl | H |
| H | 7-Cl | H |
| H | 8-F | H |
| CH$_3$ | 6-Cl | H |
| CH$_3$ | 6-Cl | 7-Cl |
| CH$_3$ | 6-CF$_3$ | H |

EXAMPLE 5

N,N-Diethyl-2-[4-(2-quinoxalinyloxy)phenoxy]-propanamide

The title compound can be prepared by interaction of 2-[4-(2-quinoxalinyloxy)phenoxy]propionic acid with thionyl chloride in a suitable solvent such as chlorobutane. Add a solution of 3.3 g (0.01 mole) 2-[4-(2-quinoxalinyloxy)phenoxy]propionyl chloride in 30 cc methylene chloride to a cold (5° C.) solution of 1.8 g (0.025 mole) diethylamine in 30 cc methylene chloride. Stir the mixture at room temperature overnight. Wash the methylene chloride solution with water and dry over magnesium sulfate. Remove the methylene chloride under vacuum to yield N,N-diethyl-2-[4-(quinoxalinyloxy)phenoxy]propanamide.

By treatment of the appropriate acid chloride with an amine using the procedure of Example 5, the amides listed in Table III can be prepared.

TABLE III

Structure: quinoxaline with substituents B, C on benzo ring, A on position 3, linked via O-phenyl-OCH(CH$_3$)-CON(R$_2$)(R$_3$)

| A | B | C | R$_2$ | R$_3$ |
|---|---|---|---|---|
| H | 6-CF$_3$ | H | H | H |
| H | 7-Br | H | H | CH$_3$ |
| H | 6-F | H | C$_6$H$_{11}$ (cyclohexyl) | H |
| H | 7-F | H | C$_6$H$_5$ | H |
| H | 6-Br | H | C$_6$H$_5$CH$_2$— | H |
| H | 7-OCH$_3$ | H | H | (CH$_3$)$_2$CH— |
| H | 7-CF$_3$ | H | t-C$_4$H$_9$ | H |
| H | 6-NO$_2$ | H | CH$_3$ | CH$_3$ |
| H | 7-Cl | 5-CH$_3$ | n-C$_4$H$_9$ | CH$_3$ |
| H | 6-CF$_3$ | 8-Cl | —(CH$_2$)$_2$—O—(CH$_2$)$_2$— | |
| H | 6-Cl | 8-Cl | —(CH$_2$)$_4$— | |
| H | 6-OCH$_3$ | 8-Cl | —(CH$_2$)$_5$— | |

TABLE III-continued

[Structure: quinoxaline with B and C substituents, A substituent, linked via O to phenyl, then OCH(CH₃)CON(R₂)(R₃)]

| A   | B     | C    | R₂       | R₃                              |
|-----|-------|------|----------|---------------------------------|
| H   | 5-Br  | 7-Br | —(CH₂)₆— |                                 |
| H   | 7-Cl  | H    | i-C₄H₉   | H                               |
| CH₃ | 6-Cl  | H    | CH₃      | CH₃O—                           |
| CH₃ | 6-Cl  | 7-Cl | C₂H₅     | H                               |
| CH₃ | 6-CF₃ | H    | H        | cyclopentyl-CH—                 |
| H   | 6-Cl  | H    | —(CH₂)₂—N(CH₃)—(CH₂)₂— |                  |
| H   | 7-Cl  | H    | H        | CH₂—CH=CH₂                      |
| H   | 7-Br  | H    | H        | CH₂CH₂N(CH₃)₂                   |
| H   | 6-Cl  | 7-Cl | CH₃      | CH₃                             |

EXAMPLE 6

Allyl 2-[4-(2-quinoxalinyloxy)phenoxy]propanoate

The following procedure can be employed to make the title compound.

To a solution of 1.2 g allyl alcohol and 1.6 g pyridine in 50 cc methylene chloride, add 6.6 g of 2-[4-(2-quinoxalinyloxy)phenoxy]propionyl chloride in 60 cc methylene chloride. Stir the mixture at room temperature overnight. Wash the methylene chloride solution with water and dry the solution over magnesium sulfate concentrate under vacuum to give allyl 2-[4-(2-quinoxalinyloxy)phenoxy]propanoate.

By treatment of the appropriate acid chloride with the appropriate alcohol, thiol, phenol or thiophenol as described above, the compounds listed in Table IV can be obtained.

TABLE IV

[Structure: quinoxaline with B and C substituents, A substituent, linked via O to phenyl, then OCH(CH₃)—C(=O)—XR₁]

| A   | B     | C    | X | R₁                  |
|-----|-------|------|---|---------------------|
| H   | 6-CF₃ | H    | O | cyclohexyl          |
| H   | 7-Br  | H    | O | —CH₂CH₂OCH₃         |
| H   | 6-Cl  | H    | O | —CH₂—C≡C—CH₂Cl      |
| H   | 7-F   | H    | O | —C₆H₅               |
| H   | 6-Br  | H    | O | —CH₂C₆H₅            |
| H   | 7-OCH₃| H    | O | —CH₂CH₂OC₂H₅        |

TABLE IV-continued

[Structure: quinoxaline with B and C substituents, A substituent, linked via O to phenyl, then OCH(CH₃)—C(=O)—XR₁]

| A   | B      | C    | X | R₁                  |
|-----|--------|------|---|---------------------|
| H   | 7-CF₃  | H    | O | —CH₂CH₂CH₂OCH₃      |
| H   | 6-NO₂  | H    | O | cyclopentyl         |
| H   | 6-CF₃  | 8-Cl | O | —CH₂C≡CH            |
| H   | 6-Cl   | 8-Cl | S | —CH₃                |
| H   | 6-OCH₃ | 8-Cl | S | —C₆H₅               |
| H   | 5-Br   | 7-Br | S | —CH₂CH=CH₂          |
| H   | 5-F    | 7-Cl | S | —CH₂C₆H₅            |
| H   | 6-Cl   | H    | S | cyclohexyl          |
| H   | 7-Cl   | H    | S | —C₂H₅               |
| H   | 8-F    | H    | S | —C₃H₇               |
| CH₃ | 6-Cl   | H    | S | —C₄H₉               |
| H   | 7-Cl   | H    | O | —CH₂—C≡C—CH₂Cl      |
| H   | 6-Cl   | 7-Cl | O | —CH₂—C≡C—CH₂Cl      |

EXAMPLE 7

2-[4-(2-Quinoxalinyloxy)phenoxy]propionitrile

The following procedure can be employed to prepare the title compound.

In a nitrogen atmosphere, add a solution of 4.9 g (0.03 mole) 2-(4-hydroxyphenoxy)propionitrile in 20 cc dimethylformamide to 1.5 g sodium hydride (0.03 mole) in 20 cc dimethylformamide. When the evolution of hydrogen ceases, add 4.9 g (0.03 mole) 2-chloroquinoxaline. Heat at approximately 130° C. until the reaction is complete. Pour into water and extract the product in ether. Dry the ethereal extracts and concentrate to yield the desired nitrile.

The compounds in Table V can be prepared in a similar fashion from the substituted 2-chloroquinoxaline and 2-(4-hydroxyphenoxy)propionitrile.

TABLE V

[Structure: quinoxaline with B and C substituents, A substituent, linked via O to phenyl, then OC(CH₃)(H)—CN]

| A   | B      | C     |
|-----|--------|-------|
| H   | 6-CF₃  | H     |
| H   | 7-Br   | H     |
| H   | 6-F    | H     |
| H   | 7-F    | H     |
| H   | 6-Br   | H     |
| H   | 7-OCH₃ | H     |
| H   | 7-CF₃  | H     |
| H   | 6-NO₂  | H     |
| H   | 7-Cl   | 5-CH₃ |
| H   | 6-CF₃  | 8-Cl  |
| H   | 6-Cl   | 8-Cl  |

TABLE V-continued

[Structure: quinoxaline with substituents B, C on benzene ring, A on position 3, linked via O to phenyl-OC(CH3)(H)-CN]

| A | B | C |
|---|---|---|
| H | 6-OCH$_3$ | 8-Cl |
| H | 5-Br | 7-Br |
| H | 5-F | 7-Cl |
| H | 6-Cl | H |
| H | 7-Cl | H |
| H | 8-F | H |
| CH$_3$ | 6-Cl | H |
| CH$_3$ | 6-Cl | 7-Cl |
| CH$_3$ | 6-CF$_3$ | H |
| C$_2$H$_5$ | 6-Cl | H |

EXAMPLE 8

Sodium 2-[4-(2-quinoxalinyloxy)phenoxy]propanoate

The following method can be employed to synthesize the sodium salt.

Add 3.1 g (0.01 mole) 2-[4-(2-quinoxalinyloxy)-phenoxy]propionic acid to a solution of 0.6 g (0.01 mole) sodium methoxide in 50 cc methanol. Stir the mixture at room temperature for 2 hours and remove the solvent under vacuum to yield the title compound.

By treatment of the appropriate carboxylic acid with a suitable base (for example, ammonia, an amine, a quaternary ammonium hydroxide, an alkali metal or an alkaline earth hydroxide, hydride, carbonate or bicarbonate) the following carboxylic acid salts may be prepared.

TABLE VI

[Structure: quinoxaline-O-phenyl-OCH(CH$_3$)CO$_2^-$ · M$^{+S}$ (salt form, $s$ subscript)]

| A | B | C | S | M |
|---|---|---|---|---|
| H | 6-CF$_3$ | H | 1 | Na |
| H | 7-Br | H | 1 | Na |
| H | 6-F | H | 1 | Na |
| H | 7-F | H | 1 | K |
| H | 6-Br | H | 1 | K |
| H | 7-OCH$_3$ | H | 1 | Li |
| H | 7-CF$_3$ | H | 1 | Li |
| H | 6-NO$_2$ | H | 1 | NH$_4$ |
| H | 7-Cl | 5-CH$_3$ | 1 | NH$_4$ |
| H | 6-CF$_3$ | 8-Cl | 1 | CH$_3$NH$_3$ |
| H | 6-OCH$_3$ | 8-Cl | 1 | (CH$_3$)$_2$NH$_2$ |
| H | 7-Cl | H | 1 | C$_4$H$_9$NH$_3$ |
| H | 8-F | H | 2 | Ca |
| CH$_3$ | 6-Cl | H | 2 | Ca |
| CH$_3$ | 6-Cl | 7-Cl | 2 | Mg |
| CH$_3$ | 6-CF$_3$ | H | 2 | Mg |

EXAMPLE 9

2-(4-Benzyloxyphenoxy)-3-methylquinoxaline

In a nitrogen atmosphere, a solution of 28.0 g (0.14 mole) 4-benzyloxyphenol in 50 cc dimethylformamide was added dropwise at about 15° C. to 6.0 g (0.14 mole) 57% sodium hydride in 25 cc dimethylformamide. When the evolution of hydrogen ceased, 25.0 g (0.14 mole) 2-chloro-3-methylquinoxaline was added and the reaction mixture was heated at 125° C. for about 2 hours. After standing overnight at room temperature, the reaction mixture was poured into ice-water (~500 cc). The solid product was filtered and crystallized from methanol or acetonitrile to give 36.3 g of the title compound, m.p. 99°-102° C.

NMR (CDCl$_3$)δ: 2.75 (s, 3H), 4.95 (s, 2H), 6.85-8.1 (m, 13H).

Following the procedure of Example 9 and by condensing the appropriate 2-chloroquinoxaline with 4-benzyloxyphenol or 4-methoxyphenol, the compounds in the following table can be prepared.

TABLE VII

[Structure: quinoxaline-O-phenyl-OCH$_2$Z]

| A | B | C | Z |
|---|---|---|---|
| H | 6-CF$_3$ | H | H |
| H | 7-Br | H | H |
| H | 6-F | H | H |
| H | 7-F | H | H |
| H | 6-Br | H | H |
| H | 7-OCH$_3$ | H | H |
| H | 7-CF$_3$ | H | H |
| H | 6-NO$_2$ | H | H |
| H | 7-Cl | 5-CH$_3$ | H |
| H | 6-CF$_3$ | 8-Cl | H |
| H | 6-Cl | 8-Cl | —C$_6$H$_5$ |
| H | 6-OCH$_3$ | 8-Cl | —C$_6$H$_5$ |
| H | 5-Br | 7-Br | —C$_6$H$_5$ |
| H | 5-F | 7-Cl | —C$_6$H$_5$ |
| H | 6-Cl | H | —C$_6$H$_5$ |
| H | 7-Cl | H | —C$_6$H$_5$ |
| H | 8-F | H | —C$_6$H$_5$ |
| CH$_3$ | 6-Cl | H | —C$_6$H$_5$ |
| CH$_3$ | 6-Cl | 7-Cl | —C$_6$H$_5$ |
| CH$_3$ | 6-CF$_3$ | H | —C$_6$H$_5$ |

EXAMPLE 10

2-(4-Hydroxyphenoxy)-3-methylquinoxaline

A solution of 12.5 g (0.05 mole) borontribromide in 100 cc methylene chloride was added, over a period of 40 minutes, to a well stirred, cold (−62° C.) solution of 17.1 g 2-(4-benzyloxyphenoxy)-3-methylquinoxaline (0.05 mole) in 400 cc methylene chloride. When the addition was complete, the temperature of the reaction was allowed to rise slowly (2 hours) to room temperature. The reaction mixture was then poured into 1 liter of water and an additional 500 cc of methylene chloride was added. The mixture was stirred vigorously for 40 minutes and the insoluble solid was filtered. Crystallization from an ethanol-water mixture (1:1) gave 6.4 g of product, m.p. 175°-178° C.

NMR (DMSO)δ: 2.8 (s, 3H), 7 (d, 2H), 7.3 (d, 2H), 7.5-8.3 (m, 4H), 9.8 (s, 1H).

The following 2-(4-hydroxyphenoxy)quinoxalines can be prepared from the appropriate ether by the procedure described above.

TABLE VIII

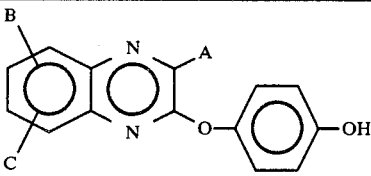

| A | B | C |
|---|---|---|
| H | 6-CF$_3$ | H |
| H | 7-Br | H |
| H | 6-F | H |
| H | 7-F | H |
| H | 6-Br | H |
| H | 7-OCH$_3$ | H |
| H | 7-CF$_3$ | H |
| H | 6-NO$_2$ | H |
| H | 7-Cl | 5-CH$_3$ |
| H | 6-CF$_3$ | 8-Cl |
| H | 6-Cl | 8-Cl |
| H | 6-OCH$_3$ | 8-Cl |
| H | 5-Br | 7-Br |
| H | 5-F | 7-Cl |
| H | 6-Cl | H |
| H | 7-Cl | H |
| H | 8-F | H |
| CH$_3$ | 6-Cl | H |
| CH$_3$ | 6-Cl | 7-Cl |
| CH$_3$ | 6-CF$_3$ | H |
| C$_2$H$_5$ | 6-Cl | H |
| C$_4$H$_9$ | 6-Cl | H |

EXAMPLE 11

Methyl 4-[4-(3-methyl-3-quinoxalinyloxy)phenoxy]pent-2-enoate

The following procedure can be used to prepare the title compound.

In a nitrogen atmosphere, add a solution of 5.4 g (0.02 mole) 2-(4-hydroxyphenoxy)-3-methylquinoxaline in 30 cc dimethylformamide to 0.9 g (0.02 mole) 57% sodium hydride in 20 cc dimethylformamide at about 20° C. When the evolution of hydrogen ceases, add 3.9 g (0.02 mole) methyl 4-bromo-2-pentenoate. Heat the reaction mixture at approximately 80° C. until the reaction is complete. Pour the reaction mixture into water and extract with ether. Combine the ethereal extracts and dry over magnesium sulfate. Removal of the ether gives the desired product.

The compounds listed in the following table can be prepared by a similar fashion from the appropriate 2-(4-hydroxyphenoxy)quinoxaline and an alkyl 4-bromo-2-pentenoate.

TABLE IX

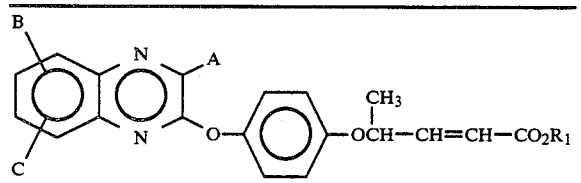

| A | B | C | R$_1$ |
|---|---|---|---|
| H | 6-CF$_3$ | H | CH$_3$ |
| H | 7-Br | H | CH$_3$ |
| H | 6-F | H | CH$_3$ |
| H | 7-F | H | CH$_3$ |
| H | 6-Br | H | CH$_3$ |
| H | 7-OCH$_3$ | H | CH$_3$ |
| H | 7-CF$_3$ | H | CH$_3$ |

TABLE IX-continued

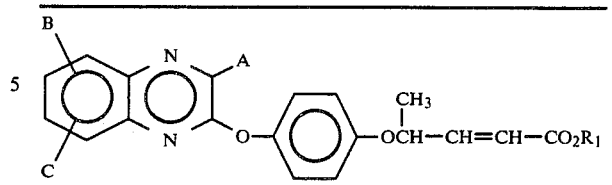

| A | B | C | R$_1$ |
|---|---|---|---|
| H | 6-NO$_2$ | H | CH$_3$ |
| H | 7-Cl | 5-CH$_3$ | n-C$_3$H$_7$ |
| H | 6-CF$_3$ | 8-Cl | CH$_3$ |
| H | 6-Cl | 8-Cl | CH$_3$ |
| H | 6-OCH$_3$ | 8-Cl | CH$_3$ |
| H | 5-Br | 7-Br | CH$_3$ |
| H | 5-F | 7-Cl | C$_4$H$_9$ |
| H | 6-Cl | H | C$_2$H$_5$ |
| H | 7-Cl | H | i-C$_3$H$_7$ |
| H | 8-F | H | t-C$_4$H$_9$ |
| CH$_3$ | 6-Cl | H | CH$_3$ |
| CH$_3$ | 6-Cl | 7-Cl | CH$_3$ |
| CH$_3$ | 6-CF$_3$ | H | CH$_3$ |
| C$_2$H$_5$ | 6-Cl | H | CH$_3$ |
| C$_4$H$_9$ | 6-Cl | H | CH$_3$ |

EXAMPLE 12

4-[4-(3-Methyl-2-quinoxalinyloxy)phenoxy]pent-2-enoic acid

The procedure described under Example 4 can be used to prepare the desired acid.

By hydrolysis of the appropriate ester, the compounds listed in Table X can be prepared.

TABLE X

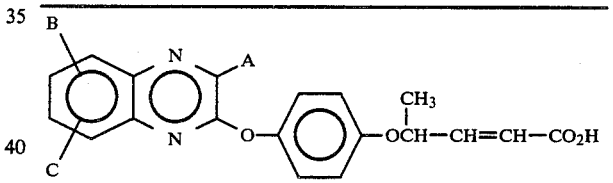

| A | B | C |
|---|---|---|
| H | 6-CF$_3$ | H |
| H | 7-Br | H |
| H | 6-F | H |
| H | 7-F | H |
| H | 6-Br | H |
| H | 7-OCH$_3$ | H |
| H | 7-CF$_3$ | H |
| H | 6-NO$_2$ | H |
| H | 7-Cl | 5-CH$_3$ |
| H | 6-CF$_3$ | 8-Cl |
| H | 6-Cl | 8-Cl |
| H | 6-OCH$_3$ | 8-Cl |
| H | 5-Br | 7-Br |
| H | 5-F | 7-Cl |
| H | 6-Cl | H |
| H | 7-Cl | H |
| H | 8-F | H |
| CH$_3$ | 6-Cl | H |
| CH$_3$ | 6-Cl | 7-Cl |
| CH$_3$ | 6-CF$_3$ | H |

EXAMPLE 13

N,N-diethyl-4-[4-(3-methyl-2-quinoxalinyloxy)phenoxy]pent-2-enamide

The method described in Example 5 can be employed to prepare the subject compound. By treatment of the appropriate acid chloride with an amine, using the procedure of Example 5, the amides listed in Table XI can be made.

TABLE XI

Structure: Quinoxaline (with substituents B, C on benzene ring, A on position 3) — O—phenyl—O—CH(CH₃)—CH=CH—CONR₂R₃

| A | B | C | R₂ | R₃ |
|---|---|---|---|---|
| H | 6-CF₃ | H | H | H |
| H | 7-Br | H | H | CH₃ |
| H | 6-F | H | cyclohexyl | H |
| H | 7-F | H | C₆H₅ | H |
| H | 6-Br | H | C₆H₅CH₂— | H |
| H | 7-OCH₃ | H | H | (CH₃)₂CH— |
| H | 7-CF₃ | H | t-C₄H₉— | H |
| H | 6-NO₂ | H | CH₃ | —CH₃— |
| H | 7-Cl | 5-CH₃ | n-C₄H₉— | —CH₃— |
| H | 6-CF₃ | 8-Cl | —(CH₂)₂—O—(CH₂)₂— | |
| H | 6-Cl | 8-Cl | —(CH₂)₄— | |
| H | 6-OCH₃ | 8-Cl | —(CH₂)₅— | |
| H | 5-Br | 7-Br | —(CH₂)₆— | |
| H | 7-Cl | H | C₄H₉— | H |
| CH₃ | 6-Cl | H | CH₃ | CH₃O— |
| CH₃ | 6-Cl | 7-Cl | C₂H₅ | H |
| CH₃ | 6-CF₃ | H | H | cyclopentyl |
| H | 6-Cl | H | —(CH₂)₂—N(CH₃)—(CH₂)₂— | |
| H | 7-Cl | H | H | CH₂—CH=CH₂ |
| H | 7-Br | H | H | CH₂CH₂N(CH₃)₂ |

EXAMPLE 14

Allyl-4-[4-(3-methyl-2-quinoxalinyloxy)phenoxy]pent-2-enoate

The method cited in Example 6 can be utilized to prepare the title compound.

The compounds listed in Table XII can be prepared in a similar fashion from the appropriate hydroxy or thio compound.

TABLE XII

Structure: Quinoxaline—O—phenyl—OCH(CH₃)—CH=CH—COXR₁

| A | B | C | X | R₁ |
|---|---|---|---|---|
| H | 6-CF₃ | H | O | cyclohexyl |
| H | 7-Br | H | O | —CH₂CH₂OCH₃ |
| H | 6-Cl | H | O | —CH₂—C≡C—CH₂Cl |
| H | 7-F | H | O | —C₆H₅ |
| H | 6-Br | H | O | —CH₂C₆H₅ |
| H | 7-OCH₃ | H | O | —CH₂CH₂OC₂H₅ |
| H | 7-CF₃ | H | O | —CH₂CH₂CH₂OCH₃ |

TABLE XII-continued

| A | B | C | X | R₁ |
|---|---|---|---|---|
| H | 6-NO₂ | H | O | cyclopentyl |
| H | 6-CF₃ | 8-Cl | O | —CH₂C≡CH |
| H | 6-Cl | 8-Cl | S | —CH₃ |
| H | 6-OCH₃ | 8-Cl | S | —C₆H₅ |
| H | 5-Br | 7-Br | S | —CH₂CH=CH₂ |
| H | 5-F | 7-Cl | S | —CH₂C₆H₅ |
| H | 6-Cl | H | S | cyclohexyl |
| H | 7-Cl | H | S | —C₂H₅ |
| H | 8-F | H | S | —C₃H₇ |
| CH₃ | 6-Cl | H | S | —C₄H₉ |
| H | 7-Cl | H | O | —CH₂—C≡C—CH₂Cl |

EXAMPLE 15

4-[4-(3-Methyl-2-quinoxalinyloxy)phenoxy]pent-2-enenitrile

The procedure described under Example 11 can be used to prepare the title compound; however, 3.3 g (0.02 mole) 4-bromo-2-pentenenitrile should be used instead of methyl 4-bromo-2-pentenoate.

In an analogous manner, the compounds in the following table can be synthesized.

TABLE XIII

Structure: Quinoxaline—O—phenyl—OCH(CH₃)—CH=CH—CN

| A | B | C |
|---|---|---|
| H | 6-CF₃ | H |
| H | 7-Br | H |
| H | 6-F | H |
| H | 7-F | H |
| H | 6-Br | H |
| H | 7-OCH₃ | H |
| H | 7-CF₃ | H |
| H | 6-NO₂ | H |
| H | 7-Cl | 5-CH₃ |
| H | 6-CF₃ | 8-Cl |
| H | 6-Cl | 8-Cl |
| H | 6-OCH₃ | 8-Cl |
| H | 5-Br | 7-Br |
| H | 5-F | 7-Cl |
| H | 6-Cl | H |
| H | 7-Cl | H |
| H | 8-F | H |
| CH₃ | 6-Cl | H |
| CH₃ | 6-Cl | 7-Cl |
| CH₃ | 6-CF₃ | H |
| C₂H₅ | 6-Cl | H |

EXAMPLE 16

Sodium 4-[4-(3-methyl-2-quinoxalinyloxy)phenoxy]pent-2-enoate

The method described under Example 8 may be used to prepare the title compound.

By treatment of the appropriate carboxylic acid with a suitable base, the following salts may be prepared.

TABLE XIV structure: B,C-substituted quinoxaline–N,A–O–phenyl–OCH(CH$_3$)–CH=CH–CO$_2^-$ · M$^{+S}$ (salt, subscript S)

| A | B | C | S | M |
|---|---|---|---|---|
| H | 6-CF$_3$ | H | 1 | Na |
| H | 7-Br | H | 1 | Na |
| H | 6-F | H | 1 | Na |
| H | 7-F | H | 1 | K |
| H | 6-Br | H | 1 | K |
| H | 7-OCH$_3$ | H | 1 | Li |
| H | 7-CF$_3$ | H | 1 | Li |
| H | 6-NO$_2$ | H | 1 | NH$_4$ |
| H | 7-Cl | 5-CH$_3$ | 1 | NH$_4$ |
| H | 6-CF$_3$ | 8-Cl | 1 | CH$_3$NH$_3$ |
| H | 6-OCH$_3$ | 8-Cl | 1 | (CH$_3$)$_2$NH$_2$ |
| H | 7-Cl | H | 1 | C$_4$H$_9$NH$_3$ |
| H | 8-F | H | 2 | Ca |
| CH$_3$ | 6-Cl | H | 2 | Ca |
| CH$_3$ | 6-Cl | 7-Cl | 2 | Mg |
| CH$_3$ | 6-CF$_3$ | H | 2 | Mg |

EXAMPLE 17

Synthesis of methyl 2-(4-hydroxyphenoxy)propanoate

A 42 g (0.25 mole) portion of methyl 2-bromopropionate was added to 0.25 mole of the sodium salt of p-benzyloxyphenol (prepared from 13.5 g sodium methoxide and 50 g p-benzyloxyphenoxy) in 70 cc of DMF. The reaction mixture was heated at approximately 80° C. for 14.5 hours. The cooled reaction mixture was then poured into 1 liter ice-water. The product was isolated by ether extraction and was crystallized from methanol to give 45.2 g methyl 2-(4-benzyloxyphenoxy)propanoate, m.p. 38°–42°.

NMR (CDCl$_3$)δ: 1.6 (d, 3H), 3.7 (s, 3H), 4.6 (q, 1H), 4.9 (s, 2H), 6.8–7 (m, 4H), 7.2–7.6 (m, 5H).

Catalytic hydrogenation at about 45 p.s.i. of 40 g of methyl 2-(4-benzyloxyphenoxy)propanoate in 200 cc DMF in the presence of 1 g of 10% Pd/c gives methyl 2-(4-hydroxyphenoxy)propanoate in almost quantitative yield. The material is of sufficient purity to be used in the preparation of the compounds of this invention.

NMR (CDCl$_3$)δ: 1.6 (d, 3H), 3.7 (s, 3H), 4.6 (q, 1H), 6.7–6.9 (m, 4H), 8 (s, 1H).

By using a halomalonic acid derivative in lieu of methyl 2-bromopropionate in the procedure of Example 17, the compounds listed in Table XV can be made. The compounds in the table which are valuable intermediates for preparing the compounds of this invention where D=CO$_2$R$_1$ and n=0, are only representative of the myriad of compounds which can be prepared by the aforementioned procedure.

TABLE XV structure: HO–phenyl–O–C(CH$_3$)(CO$_2$R$_1$)–W

| R$_1$ | W |
|---|---|
| CH$_3$ | —CN |
| n-C$_4$H$_9$ | —CON(CH$_3$)$_2$ |
| CH$_3$OCH$_2$CH$_2$— | —CON(morpholino) |
| | —CN |
| i-C$_3$H$_7$ | —CON(n-C$_4$H$_9$)(CH$_3$) |
| C$_2$H$_5$ | —CONH–phenyl |
| CH$_3$ | —CON(C$_2$H$_5$)$_2$ |
| CH$_3$ | —CON(OCH$_3$)(CH$_3$) |
| C$_2$H$_5$ | —CON(CH$_2$)$_2$N(CH$_3$)$_2$, with CH$_3$ branch |
| CH$_3$ | —CON(piperazinyl–N—CH$_3$) |

(R$_1$ = cyclohexyl for the —CN row with the cyclohexyl group shown)

EXAMPLE 18

Dimethyl 2-methyl-2-[4-(2-quinoxalinyloxy)phenoxy]propanedioate

The following procedure can be used to prepare the title compound.

In a nitrogen atmosphere, add a solution of 4.8 g (0.02 mole) 2-(4-hydroxyphenoxy)quinoxaline in 30 cc dimethylfornmamide to 0.8 (0.02 mole) 57% sodium hydride. When the evolution of hydrogen ceases, add 4.8 g (0.021 mole) dimethyl 2-bromo-2-methylpropanedioate dropwise. When the addition is complete, heat at approximately 70° C. until the reaction is complete. Pour the mixture into ice-water and extract with ether. Concentration of the dry ethereal extracts yield the title compound.

EXAMPLE 19

Methyl 2-(diethylaminocarbonyl)-2-[4-(2-quinoxalinyloxy)-phenoxy]propanoate

The procedure outlined below can be used to prepare the title compound.

In a nitrogen atmosphere, add a solution of 5.9 g (0.02 mole) methyl 2-[(dimethylamino)carbonyl]-2-(4-hydroxyphenoxy)propanoate in 30 cc dimethylformamide to 0.9 g 57% sodium hydride in dimethylformamide. When the evolution of hydrogen ceases, add 3.3 g (0.02 mole) 2-chloroquinoxaline and heat the reaction mixture at approximately ~80° C. until completion. Pour the reaction mixture into water and extract with ether. Concentration of the ethereal extracts gives the desired compound.

Following the teaching of Example 18 or 19, the compounds listed in Table XVI can be synthesized.

TABLE XVI

| A | B | C | $R_1$ | W |
|---|---|---|---|---|
| H | 6-$CF_3$ | H | $CH_3$— | CN |
| H | 7-Br | H | $CH_3$— | $CO_2CH_3$ |
| H | 7-F | H | $C_2H_5$— | —$CO_2C_2H_5$ |
| H | 7-$OCH_3$ | H | $C_3H_7$— | —$CO_2C_3H_7$ |
| H | 7-$CF_3$ | H |  | —$CONH_2$ cyclohexyl |
| H | 6-$NO_2$ | H | $C_6H_5$— | $CONH_2$ |
| H | 7-Cl | 5-$CH_3$ | $C_6H_5CH_2$ | $CON(C_2H_5)_2$ |
| H | 6-Cl | 8-Cl | n-$C_4H_9$ | CN |
| H | 5-Br | 7-Br | $CH_3$ | $CO_2CH_3$ |
| H | 5-F | 7-Cl | $CH_3$ | $CO_2CH_3$ |
| H | 6-Cl | H | $C_2H_5$ | $CONHC_4H_9$ |
| H | 7-Cl | H | $C_2H_5$ | CN |
| H | 8-F | H | $C_2H_5$ | $CO_2C_2H_5$ |
| $CH_3$ | 6-Cl | 7-Cl | $CH_3$ | CN |
| $CH_3$ | 6-$CF_3$ | H | $CH_3$ | $CO_2C_2H_5$ |
| H | 7-Br | H | $C_2H_5$ | $CONHOCH_3$ |

EXAMPLE 20

Methyl 2-methyl-2-[4-(2-quinoxalinyloxy)phenoxy]propanedioate

The procedure described under Example 4 can be used to prepare the desired acid. By hydrolysis of the appropriate diester, the compounds listed in Table XVII can be prepared.

TABLE XVII

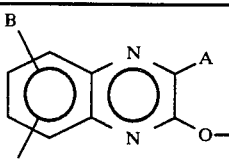

| A | B | C | $R_1$ |
|---|---|---|---|
| H | 6-Cl | H | $CH_3$— |
| H | 7-Cl | H | $CH_3$— |
| H | 6-Cl | 7-Cl | $CH_3$— |
| H | H | H | $CH_3$— |
| H | 6-F | H | $C_2H_5$— |
| H | 7-$CF_3$ | H | $C_2H_5$ |
| H | 5-Cl | H | $C_2H_5$ |
| H | 8-Br | H | $C_2H_5$ |
| $CH_3$ | 6-F | H | $CH_3$ |
| $CH_3$ | 7-Cl | H | $CH_3$ |
| $CH_3$ | 6-Cl | 7-Cl | $CH_3$ |
| $C_2H_5$ | 6-Cl | H | $CH_3$ |
| $C_4H_9$ | 6-Cl | H | $CH_3$ |

EXAMPLE 21

Sodium salt of methyl 2-methyl-2-[4-(2-quinoxalinyloxy)phenoxy]propanedioate

The procedure described under Example 8 can be utilized to prepare the sodium salts.

By careful treatment of the appropriate acid with an equimolar amount of a base, the following salts may be prepared.

TABLE XVIII

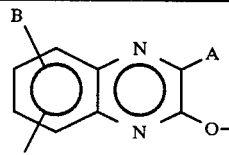

| A | B | C | $R_1$ | S | M |
|---|---|---|---|---|---|
| H | 6-Cl | H | $CH_3$— | 1 | Na |
| H | 7-Cl | H | $CH_3$— | 1 | Na |
| H | 6-Cl | 7-Cl | $CH_3$— | 1 | K |
| H | H | H | $CH_3$— | 1 | K |
| H | 6-F | H | $C_2H_5$— | 1 | Li |
| H | 7-$CF_3$ | H | $C_2H_5$ | 1 | $NH_4$ |
| $CH_3$ | 6-F | H | $CH_3$ | 1 | t-$C_4H_9NH_3$ |
| $CH_3$ | 7-Cl | H | $CH_3$ | 2 | Ca |
| $CH_3$ | 6-Cl | 7-Cl | $CH_3$ | 2 | Mg |

EXAMPLE 22

Methyl 2-methyl-3-(methylthio)-3-oxo-2[4-(2-quinoxalinyloxy)-phenoxy]propanoate

The acid chloride can be prepared by the addition of the dry sodium salt of the acid (0.1 mole) in small portions to oxalyl chloride (0.12 mole in 200 cc of ether). After 4–5 hours at room temperature, the sodium chloride is removed by filtration and the ether and excess oxalyl chloride are removed under vacuum. The crude acid chloride can be used without any further purification.

The method cited under Example 6 can be utilized to prepare the subject compound.

In an analogous manner, the compounds listed in the following table can be prepared from the acid chloride, appropriate alcohol, thiol, phenol or thiophenol.

TABLE XIX

[Structure: quinoxaline with substituents B, C on benzene ring, A on position, connected via O to phenyl bearing $CH_3$, OC—COXR$_1$, and $CO_2CH_3$ groups]

| A | B | C | X | R$_1$ |
|---|---|---|---|---|
| H | 6-Cl | H | S | $CH_3$— |
| H | 7-Cl | H | O | $C_6H_5$—$CH_2$— |
| H | 6-F | H | S | n-$C_4H_9$— |
| H | 7-Br | H | S | $CH_2$=CH—$CH_2$— |
| H | 8-Cl | H | S | $C_6H_5$ |
| H | 6-$CF_3$ | H | O | $C_6H_5$ |
| H | 8-Br | H | O | $ClCH_2C$≡C—$CH_2$— |
| H | 6-Cl | 7-Cl | O | CH≡CH—$CH_2$— |
| $CH_3$ | 6-Cl | 7-Cl | S | n-$C_4H_9$— |
| $CH_3$ | 7-Cl | H | S | $CH_3$— |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XX

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 23

Wettable Powder

| | |
|---|---|
| Methyl 2-[4-(6(or 7)-chloro-2-quinoxalinyloxy)phenoxy]propanoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 24

Wettable Powder

| | |
|---|---|
| Methyl 2-[4-(2-quinoxalinyloxy)phenoxy]propanoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 25

Granule

| | |
|---|---|
| wettable powder of Example 24 | 5% |
| attapulgite granules (U.S.S. 20-40 mesh; 0.84–0.42 mm) | 95% |

A slurry of wettable powder containing ≈25% solids is sprayed on the surface of attapulgite granules in a double-cone blender. The granules are dried and packaged.

EXAMPLE 26

Extruded Pellet

| | |
|---|---|
| Methyl 2-[4-(6,7-dichloro-2-quinoxalinyloxy)phenoxy]-propanoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 27

Oil Suspension

| | |
|---|---|
| Methyl 2-[4-(6(or 7)-chloro-2-quinoxalinyloxy)phenoxy-propanoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 28

Wettable Powder

| | |
|---|---|
| Methyl 2-[4-(2-quinoxalinyloxy)phenoxy]-propanoate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding a hammer-mill to produce particles essentially all below 100 microns, the material is reblended and sifted through a U.S.S. No. 50 sieve (0.3 mm opening) and packaged.

EXAMPLE 29

Low Strength Granule

| | |
|---|---|
| Methyl 2-[4-(6(or 7)-chloro-2-quinoxalinyloxy)phenoxy]-propanoate | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 30

Aqueous Suspension

| | |
|---|---|
| Methyl 2-[4-(2-quinoxalinyl-oxy)phenoxy]-propanoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 31

Low Strength Granule

| | |
|---|---|
| Methyl 2-[4-(6(or 7)-chloro-2-quinoxalinyloxy)phenoxy]-propanoate | 0.1% |
| attapulgite granules (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 32

Granule

| | |
|---|---|
| Methyl 2-[4-(2-quinoxalinyloxy)phenoxy]-propanoate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 33

High Strength Concentrate

| | |
|---|---|
| Methyl 2-[4-(6(or 7)-chloro-2-quinoxalinyloxy)phenoxy]-propanoate | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 34

Wettable Powder

| | |
|---|---|
| Methyl 2-[4-(2-quinoxalinyloxy)phenoxy]-propanoate | 90% |
| dioctyl sodium sulfosuccinate | 0.1% |
| synthetic fine silica | 0.9% |

The ingredients are blended and ground in a hammermill to produce particles essentially all below 100 microns. The material is sifted through a U.S.S. No. 50 screen and then packaged.

EXAMPLE 35

Wettable Powder

| | |
|---|---|
| Methyl 2-[4-(6,7-dichloro-2-quinoxalinyloxy)phenoxy]-propanoate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 36

Emulsifiable Concentrate

| | |
|---|---|
| Methyl 2-[4-(2-quinoxalinyloxy)phenoxy]-propanoate | 20% |
| chlorobenzene | 74% |
| sorbitan monostearate and polyoxyethylene condensates thereof | 6% |

The ingredients are combined and stirred to produce a solution which can be emulsified in water for application.

Compositions can contain, in addition to the active ingredients of this invention, other conventional agricultural chemicals such as fertilizers, plant growth modifiers or herbicides.

For example, the compounds of Formula I can be combined with the following herbicides:

(1) 5-tert-butyl-3-(2,4-dichloro-5-isopropoxyphenyl)-1,3,4-oxadiazol-2-one;
(2) 6-methylthio-2,4-bis(ethylamino)-s-triazine;
(3) 3-isopropyl-(1H)-benzo-2,1,3-thiodiazin-4-one-2,2-dioxide;
(4) 2,4-dichlorophenoxyacetic acid and related esters and salts;
(5) S-(2,2,3-trichloroallyl)-diisopropylthiocarbamate;
(6) Methyl 2-[4-(2,4-dichlorophenoxy(phenoxy))]-propanoate;
(7) 1,2-dimethyl-3,5-diphenyl-1H-pyrazolium methyl sulfate; and
(8) 4-chloro-2-butynyl 3-chlorocarbanilate.

The compounds of Formula I can also be combined with other herbicides and are particularly useful in combination with bromacil [3-(sec-butyl)-5-bromo-6-methyluracil], diuron [3,(3,4-dichlorophenyl)-1,1-dimethylurea], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido)-phenyl tert-butylcarbamate, 2-methyl-4-chlorophenoxyacetic acid, its salts or esters, 4-amino-6-tert-butyl-3-methylthio-as-triazine-5(4H)-one, bentazone [3-isopropyl-1H-2,1,3-benzothiadiazin-(4)-3H-one-2,2-dioxide], and linuron [3-(3,4-dichlorophenyl)-1-methoxy-1-methyl urea] for controlling a broad spectrum of weeds.

The agricultural chemicals listed above are exemplary of the compounds which can be mixed with the active compounds and are not intended to limit the invention in any way.

USE

The compounds of the present invention are useful when applied as pre- and/or post-emergence treatments for broad-spectrum control of a wide variety of weed and brush species growing on industrial sites, storage lots, along fences and building foundations, along railroad and utility rights-of-way, etc. In addition, the compounds of the invention have utility for weed control in certain crops, such as soybeans, cotton, sugarbeets and beans.

These herbicides are particularly useful for selectively removing and controlling grass weeds, including volunteer corn, in broadleaf crops including soybeans, cotton, sugarbeets, beans, flax, cabbage, tomatoes, potatoes, peanuts, carrots, cucurbits, endive, beets, etc. Grassweeds include crabgrass, barnyardgrass and wild oats. Compounds of this invention show a remarkable and unexpected degree of safety to broadleaf crops and an unusual phytotoxicity to grass weeds whether applied to the soil before seeds and crops emerge, that is, preemergence or whether applied post-emergence including spraying on the weeds and crops. In addition, the compounds are useful when applied as pre-emergence or post-emergence treatments alone and in combination with other herbicides or surfactants for broad-spectrum control of a wide variety of weeds and brush species growing on industrial sites, on storage lots and along fences, building foundations, railroad, highway and utility rights-of-way etc.

Compounds of the present invention are considered to show an unexpected degree of safety on broadleaf crops as demonstrated by use of methyl 2-[4-(6(or 7)-chloro-2-quinoxalinyloxy)phenoxy]propanoate on soybean, cotton and beans.

The precise amount of the compounds of this invention to be used in any particular situation will vary widely according to the end result desired. Factors effecting the optimum rate of application include the plant species to be controlled, soil type, formulation used, prevailing weather conditions, foliage density, length of time for which residual activity is desired, etc. Broadly speaking, the compounds are used at levels at about 0.06 to 20 kilograms per hectare, preferably approximately 0.125 to 5 kilograms per hectare. In general, the higher rates of application from within this range will be selected for adverse conditions or where extended persistence in soil is desired, and the lower rates for weed control in crops.

The herbicides effectively control grass weeds as demonstrated by the examples, but they do not control broadleaf weeds at low application rates. To obtain control of a wider spectrum of both broadleaf and grass weeds, combination treatments consisting of compounds of this invention with other herbicides effective on broadleaf weeds may be used to advantage. Combination treatments may be used with the components applied simultaneously as in a tank mix or mixed formulation, or sequentially with either or both components applied preplant incorporated, pre-emergence, post-emergence, post-emergence-directed, broadcast, band or spot treatment or any combination of these methods. The following examples of combination utility are cited:

Compounds of this invention with

| Other Herbicide | Use |
|---|---|
| bentazon (post-) | Soybeans |
| 2,4-DB (post-) | Peanuts, Soybeans Alfalfa, Clover |
| Simazin (pre-) | Nursery, Citrus, Peaches, Established Alfalfa |
| pyrazon (pre-, early post-) | Sugarbeets |
| silvex | Fence lines, rights-of-ways |
| dichloroprop (post-) | Brush, Release of Evergreens |
| MCPB (early post-) | peas |
| dicamba (pre-) | flax and rape |
| desmedipham (post-) | Sugarbeets |
| prometryn (pre-) | Celery and Cotton |
| Phenmedipham (post-) | Sugarbeets |
| acifluorofen (Blazer ®) (post-) | Soybeans |
| 2-chloro-N—[(4-methoxy-6-methyl-1,3,5-triazin-2-yl)aminocarbonyl]benzenesulfonamide | flax |
| 1-methylethyl 2[[(4,6-dimethoxy-1,3,5-triazin-2-yl)aminocarbonyl]]aminosulfonyl]]benzoate | flax |
| 1-methylethyl 2[[(4-methoxy-6-methyl-1,3,5-triazin-2-yl)aminocarbonyl]aminosulfonyl]]benzoate | flax |
| dinoseb (post-) | Soybeans |
| lenacil (pre-) | Sugarbeets |
| bromaxynil (post-) | Wheat and barley |
| fluometuron (pre-) | Cotton |
| 1-[2(([(4,6-dimethoxypyrimidin-2-yl)aminocarbonyl]-aminosulfonyl))benzoyl]-pyrrolidine | Soybeans |
| 2-propenyl(2-[[([4,6-dimethoxy-pyrimidin-2-yl)aminocarbonyl]-aminosulfonyl]]benzoate | Soybeans |

TEST A

Seeds of crabgrass (*Digitaria spp.*), barnyardgrass (*Echinochloa crusgalli*), wild oats (*Avena fatua*), *Cassia tora*, morningglory (*Ipomoea spp.*), cocklebur (*Xanthium spp.*), sorghum, corn, soybean, rice, wheat and nutsedge tubers were planted in a growth medium and treated pre-emergence with the chemicals dissolved is a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days. All species were compared to controls and visually rated for response to treatment seven and sixteen days after treatment. The ratings are based on a numerical scale extending from 0=no effect, to 10=maximum effect. The accompanying descriptive symbols have the following meanings:

S=albanism;
G=growth regardation;
C=chlorosis/necrosis;
E=emergence inhibition; and
H=formative effects.

The ratings for the compound tested by this procedure are shown in Table A for 16 days after treating.

TABLE A

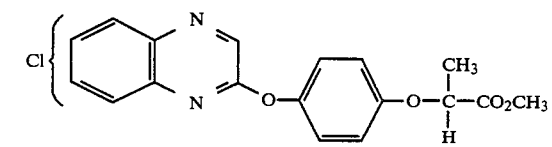

| kg/ha | 2 | 0.1 |
|---|---|---|
| POST-EMERGENCE | | |
| BUSHBEAN | 1S | 0 |
| COTTON | 2C | 0 |
| MORNINGGLORY | 2C | 0 |
| COCKLEBUR | 1C,5G | 0 |
| CASSIA | 0 | 0 |
| NUTSEDGE | 0 | 0 |
| CRABGRASS | 10C | 10C |
| BARNYARDGRASS | 10C | 10C |
| WILD OATS | 10C | 10C |
| WHEAT | 9C | 10C |
| CORN | 10C | 10C |
| SOYBEAN | 1C,3G | 0 |
| RICE | 10C | 10C |
| SORGHUM | 10C | 10C |
| PRE-EMERGENCE | | |
| MORNINGGLORY | 0 | 0 |
| COCKLEBUR | 4G | 0 |
| CASSIA | 0 | 0 |
| NUTSEDGE | 0 | 0 |
| CRABGRASS | 10E | 10E |
| BARNYARDGRASS | 10E | 10E |
| WILD OATS | 5C,9G | 8G |
| WHEAT | 10E | 10E |
| CORN | 10H | 7C,9G |
| SOYBEAN | 0 | 0 |
| RICE | 10E | 10E |
| SORGHUM | 10E | 10C |

What is claimed is:

1. A compound of the formula:

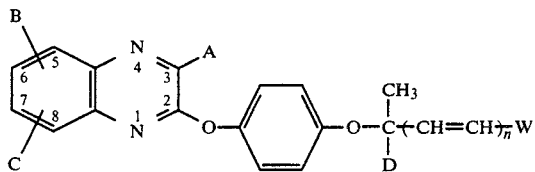

where

A is H or $C_1$-$C_4$ alkyl;

B is H, Cl, Br, F, $CF_3$, $OCH_3$ or $NO_2$;

C is H, $CH_3$, Cl, Br or F;

W is CN or

R is Cl, $XR_1$, $NR_2R_3$, OH or OM;

$R_1$ is $C_1$-$C_4$ alkyl,

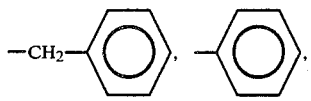

$C_5$-$C_8$ cycloalkyl, —$CH_2CH_2OCH_3$, —$CH_2CH_2OCH_2CH_3$ or —$CH_2CH_2CH_2OCH_3$, $C_3$-$C_4$ alkenyl, $C_3$-$C_4$ alkynyl or $C_3$-$C_4$ alkenyl or alkynyl optionally substituted with one Cl;

X is O or S;

M is an agriculturally suitable salt;

$R_2$ is H, $C_1$-$C_4$ alkyl, $C_5$-$C_8$ cycloalkyl

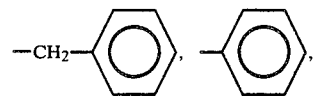

$OCH_3$, $C_3$-$C_4$ alkenyl, or —$CH_2CH_2NR_4R_5$ where $R_4$ and $R_5$ are independently methyl or ethyl;

$R_3$ is H or $C_1$-$C_4$ alkyl; or $R_2$ and $R_3$ may be taken together to be —$(CH_2)_2$—O—$(CH_2)_2$—, —$(CH_2)_4$—, —$(CH_2)_5$— or —$(CH_2)_6$— or

—$(CH_2)_2$—N—$(CH_2)_2$—;
  |
  $CH_3$ n is 0 or 1;

D is H, or $C_2R_1$;

provided that:

(a) when n=1, then D=H; and (b) $R_2$ and $R_3$ together contain no more than 6 carbon atoms (c) when n is O, A is $C_1$-$C_4$ alkyl.

2. A compound of claim 1 wherein A is H or $CH_3$.

3. A compound of claim 2 where A is H.

4. A compound of claim 3 where B and C are independently H, F, Cl or Br.

5. A compound of claim 4 where B and C are at positions 6 and 7 of the quinoxaline ring.

6. A compound of claim 5 where R is $OR_1$, OH or OM.

7. A composition for the control of undesirable vegetation consisting essentially of a herbicidally effective amount of a compound of any of claims 1–6 and at least one of (a) a surface active agent and (b) a solid or liquid diluent.

8. A method for the control of undesirable vegetation comprising applying to the locus of such undesirable vegetation a herbicidally effective amount of a compound of any of claims 1–6.

9. A method for the control of grass weeds in broadleaf crops comprising applying to the locus of such grass weeds a herbicidally effective amount of a compound of any of claims 1 to 6.

* * * * *

UNITED STATES PATENT AND TRADEMARK OFFICE
CERTIFICATE OF CORRECTION

PATENT NO. : 4,609,396
DATED : September 2, 1986
INVENTOR(S) : Maged M. Fawzi

It is certified that error appears in the above—identified patent and that said Letters Patent is hereby corrected as shown below:

Column 32, line 19, delete "$C_2R_1$" and substitute -- $CO_2R_1$ --.

Signed and Sealed this

Seventh Day of April, 1987

Attest:

DONALD J. QUIGG

*Attesting Officer*     *Commissioner of Patents and Trademarks*